US012721862B2

(12) United States Patent
Pizzocaro et al.

(10) Patent No.: US 12,721,862 B2
(45) Date of Patent: Sep. 1, 2026

(54) PHARMACEUTICAL COMPOSITION FOR USE IN THE TREATMENT OF CYSTITIS OF VARIOUS ETIOLOGIES

(71) Applicant: FIDIA FARMACEUTICI S.P.A., Abano Terme (IT)

(72) Inventors: Carlo Pizzocaro, Abano Terme (IT); Anna Maria Zanellato, Abano Terme (IT); Mauro Pavan, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 775 days.

(21) Appl. No.: 17/766,872

(22) PCT Filed: Oct. 22, 2020

(86) PCT No.: PCT/IB2020/059922

§ 371 (c)(1),
(2) Date: Apr. 6, 2022

(87) PCT Pub. No.: WO2021/079303

PCT Pub. Date: Apr. 29, 2021

(65) Prior Publication Data

US 2024/0075054 A1 Mar. 7, 2024

(30) Foreign Application Priority Data

Oct. 24, 2019 (IT) ........................ 102019000019762

(51) Int. Cl.
*A61K 31/728* (2006.01)
*A61K 9/00* (2006.01)

(52) U.S. Cl.
CPC .......... *A61K 31/728* (2013.01); *A61K 9/0034* (2013.01)

(58) Field of Classification Search
CPC ............................ A61K 31/728; A61K 9/0034
See application file for complete search history.

(56) References Cited

U.S. PATENT DOCUMENTS

| | | | | |
|---|---|---|---|---|
| 5,888,986 A * | 3/1999 | Morales | A61P 13/10 | 514/777 |
| 2012/0245080 A1* | 9/2012 | Goolsbee | A61P 37/06 | 435/375 |
| 2013/0251785 A1* | 9/2013 | Lander | A61K 9/0034 | 514/56 |
| 2017/0020912 A1* | 1/2017 | Drizen | A61K 45/06 | |
| 2017/0020913 A1* | 1/2017 | Pilotto | A61K 9/122 | |

FOREIGN PATENT DOCUMENTS

| | | |
|---|---|---|
| CA | 2 347 110 A1 | 5/2000 |
| WO | WO 99/24070 A2 | 5/1999 |

OTHER PUBLICATIONS

Huang, W., Wang, F., Wu, C., & Hu, W. (2015). Efficacy and safety of pirarubicin combined with hyaluronic acid for non-muscle invasive bladder cancer after transurethral resection: a prospective, randomized study. International urology and nephrology, 47, 631-636. (Year: 2015).*
International Search Report, issued in PCT/IB2020/059922, PCT/ISA/210, dated Jan. 22, 2021.
Sanzgiri et al., "Evaluation of mucoadhesive properties of hyaluronic acid benzyl esters", International Journal of Pharmaceutics, vol. 107, (1994), p. 91-97.
Waddell et al., "The Use of Hyaluronan After Arthroscopic Surgery of the Knee", The Journal of Arthroscopic and Related Surgery, vol. 26, No. 1, Jan. 2010, p. 105-111.
Written Opinion of the International Searching Authority, issued in PCT/IB2020/059922, PCT/ISA/237, dated Jan. 22, 2021.

* cited by examiner

*Primary Examiner* — Scarlett Y Goon
*Assistant Examiner* — David H Cho
(74) *Attorney, Agent, or Firm* — Birch, Stewart, Kolasch & Birch, LLP

(57) ABSTRACT

A pharmaceutical sterile composition consisting of hyaluronic acid sodium salt and Hyaff11p50 and related use in the intravesical treatment of interstitial cystitis or Bladder Pain Syndrome (IC/BPS), of acute cystitis following bacterial infection, trauma or urolithiasis, of cystitis caused by radiation, chemotherapy, and hemorrhagic cystitis, as well as in the treatment of the bladder of patients undergoing endoscopic resection of benign or malignant bladder tumour at risk of relapse, are described.

14 Claims, 1 Drawing Sheet

*: p < 0,05; n=3 (Student's t-test : CTRL vs Sample A)
#: p < 0,05; n=3 (Student's t-test : Sample B vs Sample A)

PHARMACEUTICAL COMPOSITION FOR USE IN THE TREATMENT OF CYSTITIS OF VARIOUS ETIOLOGIES

OBJECT OF THE INVENTION

The present invention discloses a pharmaceutical composition for use in the treatment of cystitis having various etiologies.

An object of the invention is a pharmaceutical sterile composition comprising, or consisting of, hyaluronic acid sodium salt and Hyaff11p50, wherein hyaluronic acid sodium salt has a concentration equal to 1.8% w/w and Hyaff11p50 has a concentration equal to 0.2% w/w, said Hyaff11p50 being the benzyl ester of hyaluronic acid wherein 50% of HA carboxyl groups is esterified with hydroxy groups of benzyl alcohol, possibly in presence of pharmacologically acceptable excipients. A further object is the above-mentioned composition for use in the intravesical treatment of interstitial cystitis or Bladder Pain Syndrome (IC/BPS), of acute cystitis following bacterial infection, trauma or urolithiasis, of cystitis caused by radiation, chemotherapy, and hemorrhagic cystitis; lastly the above-mentioned composition for use by administration by intravesical instillation in the treatment of the bladder of patients undergoing endoscopic resection of benign or malignant bladder tumour at risk of relapse.

FIELD OF THE INVENTION

Bladder tumours originate on the inner bladder mucosa placed in direct contact with urine, the most common form being a papilloma, an isolated, superficial tumour similar to a small wart. Malignant bladder tumours usually form from its epithelial tissue and are therefore carcinomas. Most of these tumours are represented by transitional (or urothelial) carcinomas since they originate from the transitional epithelium, squamous cell bladder carcinoma and adenocarcinomas being much rarer.

The tumour that invades the detrusor muscle is defined as a muscle-invasive carcinoma (MIBC) since it has a tendency to metastasize spreading to the lymph nodes and other organs, although about 75-80% of the newly diagnosed patients have a non muscle-invasive bladder carcinoma (NMIBC) which may be classified as:

- Ta, papillary carcinoma confined to the mucosa surface (about 70% of the NMIBCs) with a low degree of malignancy such as to be considered (according to some guidelines) a non-malignant form of bladder tumour.
- Tl, a papillary carcinoma that crosses the mucosa (about 20% of the NMIBCs)
- CIS (Carcinoma In Situ) a flat tumour confined to the mucosa, often multifocal (about 10% of the NMIBCs) with a high degree of anaplasia is considered a precursor of muscle-invasive carcinoma.

The most common symptom of bladder tumour is haematuria (blood in the urine), visible to the naked eye, although the suspicion of a bladder carcinoma should also arise in patients with non-specific symptoms (affecting the lower urinary tract) associated with an increase in the urge to urinate and its frequency with dysuria (difficult emission of urine). Diagnostic confirmation is obtained by histological examination by transuretal biopsy.

Treatment standards both of benign bladder tumours and carcinomas is the resection of the bladder tumour by transuretal endoscopy (TURBT). This endoscopic surgery may be followed by intravescical instillations of chemotherapeutic drugs such as, for example, Mitomycin C or immunotherapies such as the *Bacillus* Calmette-Guérin (BCG). To date, the treatment with BCG represents the best therapy for Carcinoma In Situ (CIS). The scope of the instillations is the prevention of relapses which occur at a rate of 30-60% and that require monitoring of the patient for at least 5 years.

Risk classification of post-operative relapse and progression of the disease obtained by histological examination allows to define the suitability of the following adjuvant treatments:

- patients with low relapse risk receive a single perioperative dose of intravesical chemotherapeutic agent within the first hours from TURBT surgery;
- patients with intermediate risk of relapse and low risk of progression are subjected to a single perioperative dose of intravesical chemotherapeutic agent, followed by adjuvant therapy based on intravesical instillations of chemotherapeutic or immunotherapeutic agents (BCG);
- patients with a high risk of progression (particularly with CIS) are always subjected to intravesical adjuvant therapy with BCG.

Most of the patients operated for NMIBC-type tumour has at least one relapse in the 5 years following removal of the tumour (normally by TURBT), and often this type of carcinoma turns into MIBC originating metastases.

The extracellular matrix is the main barrier to the invasion/migration of tumour cells vs other organs/tissues, and the matrix metalloproteases (MMPs) are among the main enzymes responsible for such metastatic spread: they consist of a wide family of proteolytic enzymes (calcium-dependent endopeptidases), being highly involved in the remodeling and degradation of such extracellular matrix (Faba O. et al., ISNR Urology, 2012, 2012:581539). MMP2, MMP7 and MMP9 are considered as the most relevant MMPs in the bladder carcinoma which are capable of defining the power/capability of spreading of tumour cells as being highly effective in degrading the basal membrane of the bladder mucosa. MMP2, MMP7 and MMP9 are then highly involved in the initial steps of metastasis since promoting tumour cells dissemination by disrupting matrix integrity (Bolenz C. et al., Bladder Cancer, 2018, 4: 67-75; Fouad H. et al., J Biochem Mol Toxicol, 2019, (33)4).

It should be highlighted that in vitro test with human bladder carcinoma cells wherein the genetic and protein expression of MMP7 has been reduced by using siRNA, caused the significant reduction of metastatic spread capability of the treated tumour cells themselves (Bolenz C. et al., Bladder Cancer, 2018, 4: 67-75). The extracellular matrix is composed by two main classes of macromolecules: polysaccharides belonging to the class of glycosaminoglycans (GAGs), and the fibrous proteins. GAGs are usually bound to proteins to form proteoglycans, they can be rich in sulfate groups such as chondroitin sulfate, dermatan sulfate, heparan sulfate and keratan sulfate, or being sulfate groups-free such as hyaluronic acid. Also fibrous protein comprise two groups: one mainly having a structural function wherein collagen and elastin can be found, and one mainly having adhesive functions wherein fibronectin, laminin and vitronectin can be found.

MMP7 is the smaller enzyme of the above-mentioned family (28 kDa), being active vs several matrix components such as laminin, fibronectin, elastin, VE-cadherin and type IV collagen, whereas MMP9 belongs to the class of gelatinases which is capable of degrading gelatin, fibronectin, elastin and various type of collagen (IV, V, VII, X, XIV), as well as proteoglycans.

High concentrations of MMP7 and MMP9 have been measured not only in serum, urine and tissues of patients suffering from bladder carcinoma (Szarvas T. et al., Cancer Science, 2010, 101, 5: 1300-1308), but were also detected in the mucosae and urines of not tumour pathological bladders which, however, showed a situation of strong inflammation such as in the case of acute cystitis from infection or trauma or urolithiasis, cystites caused by radiations or chemotherapy, hemorrhagic cystitis and interstitial cystitis (Ambite I. et al., PLOS Pathogens, 2016, 12(10); Chen Y. et al., Am J Transl Res, 2014, 6(6):631-648).

Interstitial cystitis IC, also defined as Bladder Pain Syndrome BPS is a pathological condition of chronic painful inflammation of the bladder wall, the origins of which is still partially unknown. It is associated with a series of strongly disabling symptoms that can negatively affect patients' lifestyle: a painful need to urinate with an increase in its frequency, pelvic pain, dysuria. It has been proven that this pathology is mainly related to a bladder epithelium dysfunction: its surface shows indeed a coating layer formed mainly by two types of molecules, glycoproteins and glycosaminoglycans (GAG) that form an impenetrable barrier that protects the bladder from irritating agents present in urine. The alteration of these two macromolecular components allows the epithelium of the bladder to contact the substances contained in the urine triggering a series of events (including mast cells degranulation and synthesis of inflammatory agents such as metalloproteases) that determine an inflammatory process of the bladder with depolarization of the fibers afferent to the bladder and the resulting onset of pelvic pain (Porru D. et al., Int. Urogynecol J, 2012, 23:1193-1199).

The intravesical instillation of hyaluronic acid (HA) appears to promote the regeneration of epithelial GAGs, in fact the now ten-year clinical use of this polysaccharide in the treatment of IC/BPS cystitis has demonstrated how such a medicament determines a clear reduction in the above-mentioned symptoms. Therefore there are several HA-based products used in the topical treatment of cystitis for the re-epithelization of the bladder mucosa: high molecular weight (MW) HA such as Cystistat®, or low molecular weight HA such as Uromac® and HYACYST®, a HA-based pharmaceutical composition with chondroitin sulphate such as Ialuril® or only based on chondroitin sulphate such as Uracyst®.

HA is a heteropolysaccharide composed by residues of d-glucuronic acid and N-acetyl-D-glucosamine. It is a linear chain polymer with a variable molecular weight between 50.000 and $13\times10^6$ Da, depending on the source from which it is obtained and the method of preparation employed. It is present in nature in pericellular gel, in the fundamental substance of connective tissue of vertebrate organisms (of which it represents one of the main components), in synovial joint fluid, in vitreous fluid and in the umbilical cord. HA plays a key role in the tissue repair process both from a structural point of view (in the organization of the extracellular matrix and in the regulation of its hydration) as well as a stimulant substance of a wide range of processes in which it acts directly or indirectly (clot formation, phagocytic activity, proliferation of fibroblasts, neovascularization, re-epithelization, etc.) (Weigel P. et al., J Theoretical Biol, 1986:219-234). Such properties have long been exploited in the preparation of medications to cure wounds, ulcers, and cutaneous lesions of various nature, dermal fillers and as viscosupplements in the lubrication of osteoarthrosic joints.

The treatment of bladder tumour, (both benign and malignant) is one of the most expensive due to the high percentages of relapse that require intensive surveillance strategies with regular reviews (cystoscopy, blood tests and urinalysis).

In particular, the management of non-muscle invasive tumours (NMIBC) is more expensive than that of invasive tumours (MIBC) due to the high rate of local relapses involving a repetition of endoscopic resection and screening, as well as the intravesical instillation of chemotherapeutic and immunotherapeutic drugs.

In Italy the annual cost for the management of this disease represents 7% of the entire national health expenditure because bladder tumour is the fifth tumour in the Western world for incidence and the second among the urinary tract tumours after prostate carcinoma.

Scientific research in these last few years has identified in the expression of specific metalloproteases (amongst others MMP7 and MMP9) in the bladder epithelium of patients undergoing TURBT, the main tumor biomarkers capable of indicating the probability of relapses; MMP7 and MMP9 therefore represent an important therapeutic target since the development of drugs that may assist in the lowering and/or inhibition of their gene and/or protein expression would open new possibilities for treatment of the benign forms of tumour as well as the above-mentioned bladder carcinomas and a new therapy for the treatment of bladder inflammation (wherein MMPs are heavily involved) characterizing acute cystitis, cystitis caused by radiations or chemotherapy, hemorrhagic cystitis but mainly as a treatment of interstitial cystitis.

DETAILED DESCRIPTION OF THE INVENTION

Figure 1:
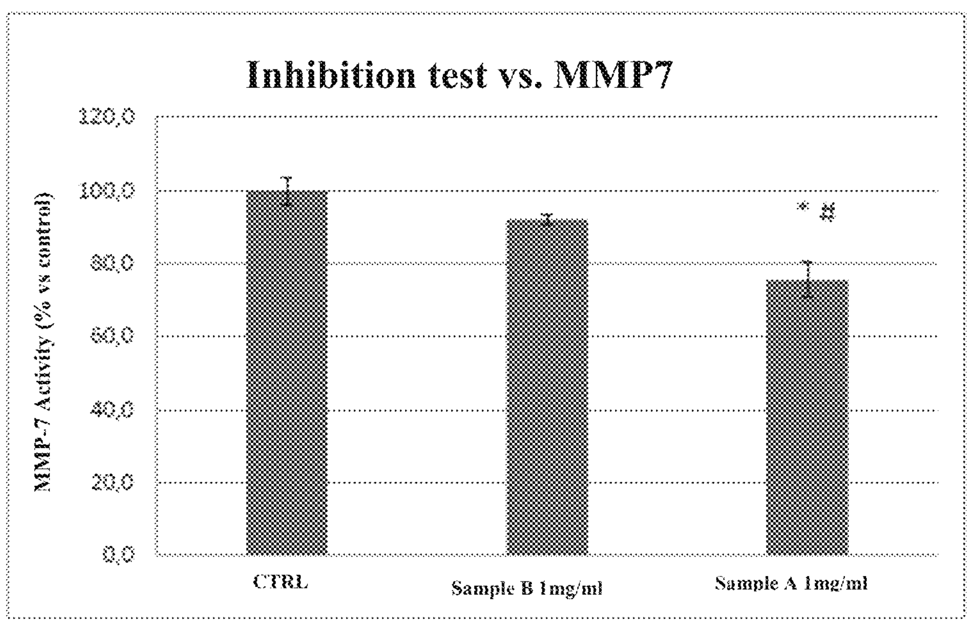
FIG. 1 is a graph illustrating the superiority of the composition object of the present invention (sample A) in the inhibition ability of MMP7 versus PBS control in which no inhibitor was present and versus sample B represented by HA sodium salt, the concentration being equal.

An object of the present invention is a pharmaceutical sterile composition comprising, or consisting of, hyaluronic acid sodium salt and Hyaff11p50, where hyaluronic acid sodium salt has a concentration equal to 1.8% w/w and Hyaff11p50 has a concentration equal to 0.2% w/w, said Hyaff11p50 being the benzyl ester of hyaluronic acid wherein 50% of HA carboxyl groups is esterified with hydroxy groups of benzyl alcohol, possibly in presence of pharmacologically acceptable excipients.

In the preferred embodiment of the invention, the hyaluronic acid of both the components of the above-mentioned pharmaceutical sterile composition (i.e. HA sodium salt and Hyaff11p50) has an average MW in the range between 160 and 260 kDa.

An object of the present invention is also the above-mentioned pharmaceutical composition for use in the intravesical treatment of interstitial cystitis (IC/BPS), of acute cystitis following bacterial infection, trauma or urolithiasis, of cystitis caused by radiation, chemotherapy, and hemorrhagic cystitis.

A further object of the invention is the above-mentioned pharmaceutical composition for use in the intravesical treatment of the bladder of patients undergoing endoscopic resection of benign or malignant bladder tumour at risk of relapse.

All the intravesical treatments are preferably carried out by administration by instillation by catheter.

In fact, the Applicant has surprisingly found and subsequently demonstrated that the pharmaceutical composition consisting of hyaluronic acid sodium salt and Hyaff11p50 in the above weight ratios, is effective in significantly inhibiting the activity of vesical MMPs, particularly MMP7 and MMP9.

As widely described above, MMP7 and MMP9 are expressed/present in the mucosa and/or urine of bladders affected by cystitis (having various etiologies) where they disrupt the GAG coating of the urothelium and contribute to the mucosal inflammation, which in the tissues of bladders undergone to tumour removal by TURBT wherein they degrade the main components of the extracellular matrix promoting the relapses that, therefore, can transform into metastasis.

The pharmaceutical sterile composition consisting of HA sodium salt and Hyaff11p50 described above has the biological and physical-chemical properties as summarized below:

- HA of both the components of the described pharmaceutical composition has a MW in the range between 160 and 260 kDa (measured after sterilization, such measurement provides the average MW of the total HA present in the above-mentioned pharmaceutical composition): this specific fraction of MW, defined in the literature as low MW, is capable of stimulating cell proliferation in a higher percentage than other fractions of HA of different MW and then is capable of enhancing the repair of the bladder epithelium damaged by the toxic/irritating substances present in the urine of patients suffering from IC, or injured in its integrity by TURBT surgery;
- Hyaff11p50 has a hydrating effect more effective and durable compared to HA, thus contributing to improve the healing of the bladder;
- both the polysaccharides contribute to the reconstruction of the surface barrier of bladder mucosa (GAG layer) to make it impermeable to urine toxins again;
- but, especially, as claimed above, the composition object of the invention is effective in significantly inhibiting the activity of MMP7 and MMP9 expressed/present in bladder tissues of bladders being pathological for IC/BPS and TURBT surgery.

The starting HA used in the present invention can be from any source: by extraction from cockscombs (e.g. according to EP138572), by fermentation (from *Streptocuccus equi* or *Zooepidemicus*, e.g. according EP0716688), or biosynthesis (from *Bacillus*, e.g. according EP2614088 and EP2614087), and it can be purified and produced as sodium salt as known by the skilled person, e.g. according to EP3491027 and WO2019016699; it is preferable using starting HA of fermentative origin. The preparation of the ester derivative Hyaff11p50 occurs as known to the skilled person, preferably according to EP0216453, even more preferably according to EP3074023 wherein the synthesis thereof from a HA having an average MW of 200 kDa is described.

It should be highlighted that molecular weight or average molecular weight of HA means the weight average molecular weight calculated by the "intrinsic viscosity" method (Terbojevich et al., Carbohydr Res, 1986, 363-377).

The pharmaceutical composition object of the invention is preferably autoclaved at 121° C. for 12-15 minutes, as well known to the skilled person.

The pharmaceutical composition can possibly contain, in addition to the ordinary pharmaceutically acceptable excipients for intravesical administration, pharmaceutically active substances such as, for example, anesthetics or anti-inflammatories.

Example 1

Preparation of the Pharmaceutical Sterile Composition Consisting of Hyaluronic Acid Sodium Salt, 1.8% w/w, and Hyaff11p50, 0.2% w/w 97.2 g of distilled water were weighed into a glass beaker. 0.75 g of Euxyl PE9010 (preservative excipients: phenoxyethanol and ethylhexylglycerin) were added under stirring by using blade mechanical stirrer, and left until complete solubilization.

5.5 mg of a 50% lactic acid solution (pH adjusting excipient) were added and pH was measured for verifying that it was comprised between 3.0 and 4.0.

Then, 0.2 g of HYAFF11p50 (prepared according to EP3074023) were added under stirring, until complete dissolution. The solution was then filtered on a 200 mesh sieve.

The solution was stirred again and 1.8 g of hyaluronic acid (prepared by fermentation from *Streptococcus equi* and purified according to EP3491027) were added and left under stirring until the whole solution obtained was homogeneous by visual inspection. The pH was checked again, verifying that it was comprised between 5.0 and 5.5; the pH was equal to 5.4.

The thus obtained solution was transferred into syringes of the desired volume and autoclaved at 121° C. for 12 minutes. At the end of the sterilization the average MW was measured according to Terbojevich et al. and it was in the range between 160 and 260 kDa.

Example 2

Inhibition Test Vs MMP9 and MMP7

Two samples were prepared for such test:

- Sample A: sterile composition prepared according to Example 1 consisting of hyaluronic acid sodium salt, 1.8% w/w, and Hyaff11p50, 0.2% w/w;
- Sample B: sterile solution of hyaluronic acid sodium salt 2% w/w having an average MW equal to 200 kDa prepared according to Example 1 except for Hyaff11p50 (not present); (in order to carry out the suitable control vs sample A, the sample B has a final concentration of HA equal to 2% since the Hyaff is a HA derivative and, therefore, the two concentrations of HA were summed).

The two samples are the two solutions to be tested in order to verify the possible inhibition of MMP enzymes; an inhibitor solution was then prepared for each sample:

Inhibitor solution: 0.25 ml of sample A or B were transferred to a glass tube to which, subsequently, 0.75 ml of PBS 0.1M pH 7.0 were added.

The entire process was carried out following the instructions as reported in the manual of the kit (MMP inhibitor profiling kit, BML-AK016, Enzo Life Science):

MMP9 and MMP7 were thawed and diluted 1/60 (MMP9) or 1/70 (MMP7) in assay buffer, the substrate was diluted 1/10 in assay buffer as well;

50 μl of assay buffer were added to each well, 20 μl of PBS (control) 0.1M pH 7.0, or 20 μl of the inhibitor solution A or B, and 20 μl of enzyme MMP7 or MMP9 diluted as above; for the PBS control and for both the samples the test was carried out with n=4;

the plate was then covered with an adhesive strip and placed at 37° C. under orbital shaking for 28 minutes;

at the end of the incubation, 10 μl of substrate were added to each well to a well final volume of 100 μl.

The plate was then placed into the microplate reader Tecan Infinite Pro M200, where fluorescence was read (λex: 328 nm; λem:420 nm; gain:80) at 1'30" intervals for a total of 35 minutes. At the end of the kinetic reaction, for each sample the substrate hydrolysis initial rate (ir) was obtained by fitting the data with a first order kinetics (fluorescence intensity (RFU) vs time (s)); therefore, the average, the standard deviation and the standard error of the replicates performed were calculated for each sample. The averages of inhibition rates of the tested pharmaceutical composition were normalized versus the control (well containing the enzyme with PBS, therefore without inhibitor) considering the latter with an activity equal to 100%. The averages of the inhibition rates of samples A, B and the control were compared by the Student's t-test for the statistical significance ($p<0.05$).

Figure 2:
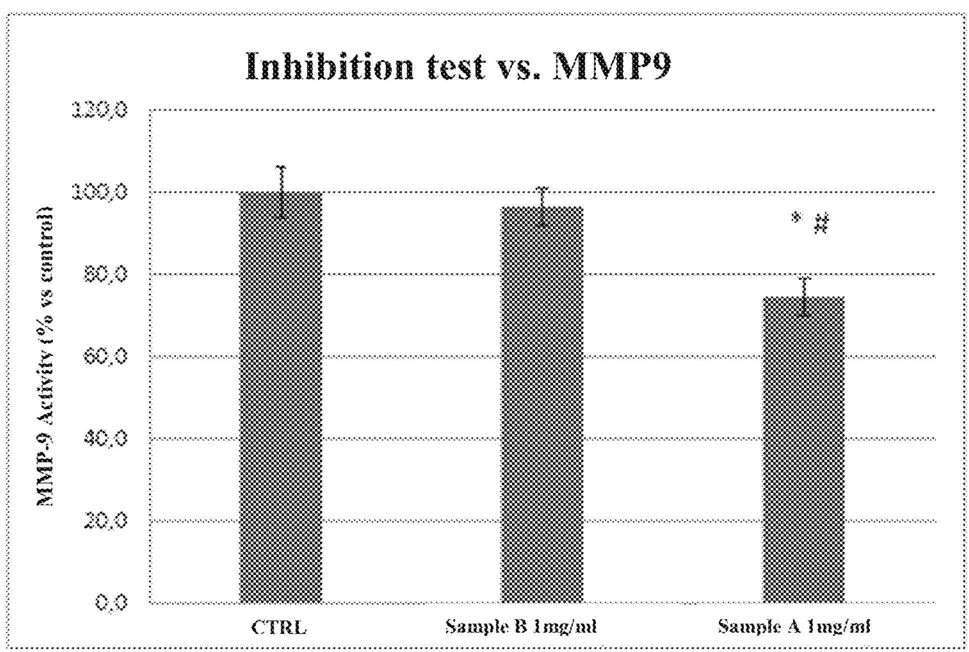
FIG. 2 is a graph illustrating the superiority of the composition object of the present invention (sample A) in the inhibition ability of MMP9 versus PBS control in which no inhibitor was present and versus sample B represented by HA sodium salt, the concentration being equal.

FIGS. 1 and 2 show the superiority of the composition object of the present invention (sample A) in the inhibition ability of MMP7 and MMP9 both vs PBS control in which, therefore, no inhibitor was present, and vs sample B represented by HA sodium salt, the concentration being equal, and such inhibition is significant in both cases.

The invention claimed is:

1. A pharmaceutical sterile composition comprising hyaluronic acid sodium salt;

Hyaff11p50, wherein the hyaluronic acid sodium salt has a concentration equal to 1.8% w/w and the Hyaff11p50 has a concentration equal to 0.2% w/w, wherein Hyaff11p50 is a benzyl ester of hyaluronic acid with 50% of HA carboxyl groups esterified with hydroxy groups of benzyl alcohol; and optionally pharmacologically acceptable excipients-, wherein hyaluronic acid of both the hyaluronic acid sodium salt and the Hyaff11p50 has an average MW in the range between 160 and 260 kDa.

2. The pharmaceutical sterile composition according to claim 1, consisting of hyaluronic acid sodium salt, Hyaff11p50, and pharmacologically acceptable excipients, wherein the hyaluronic acid sodium salt has a concentration equal to 1.8% w/w and the Hyaff11p50 has a concentration equal to 0.2% w/w, wherein said Hyaff11p50 is a benzyl ester of HA with 50% of HA carboxyl groups esterified with hydroxy group of benzyl alcohol.

3. A method of intravesical treatment of interstitial cystitis or Bladder Pain Syndrome, of acute cystitis following bacterial infection, trauma or urolithiasis, of cystitis caused by radiation, chemotherapy, and hemorrhagic cystitis, which comprises administering to a patient in need thereof the composition according to claim 1.

4. The method according to claim 3, wherein said composition is administered by instillation by catheter.

5. A method of intravesical treatment of the bladder of patients undergoing endoscopic resection of benign or malignant bladder tumour at risk of relapse, which comprises administering to a patient in need thereof the composition according to claim 1.

6. The method according to claim 5, wherein said composition is administered by instillation by catheter.

7. A method of intravesical treatment of interstitial cystitis or Bladder Pain Syndrome, which comprises administering to a patient in need thereof the composition according to claim 1.

8. The method according to claim 7, wherein said composition is administered by instillation by catheter.

9. A method of intravesical treatment of the bladder of patients undergoing endoscopic resection of bladder tumour at risk of relapse, which comprises administering to a patient in need thereof the composition according to claim 1.

10. The method according to claim 9, wherein said composition is administered by instillation by catheter.

11. A method of intravesical treatment of interstitial cystitis or Bladder Pain Syndrome, of acute cystitis following bacterial infection, trauma or urolithiasis, of cystitis caused by radiation, chemotherapy, and hemorrhagic cystitis, which comprises administering to a patient in need thereof the composition according to claim 1.

12. A method of intravesical treatment of the bladder of patients undergoing endoscopic resection of benign or malignant bladder tumour at risk of relapse, which comprises administering to a patient in need thereof the composition according to claim 1.

13. A method of intravesical treatment of interstitial cystitis or Bladder Pain Syndrome, of acute cystitis following bacterial infection, trauma or urolithiasis, of cystitis caused by radiation, chemotherapy, and hemorrhagic cystitis, which comprises administering to a patient in need thereof the composition according to claim 2.

14. A method of intravesical treatment of the bladder of patients undergoing endoscopic resection of benign or malignant bladder tumour at risk of relapse, which comprises administering to a patient in need thereof the composition according to claim 2.

* * * * *